(12) United States Patent
Todaro et al.

(10) Patent No.: US 6,204,364 B1
(45) Date of Patent: Mar. 20, 2001

(54) HYBRID CYTOKINES

(75) Inventors: George J. Todaro; Timothy M. Rose, both of Seattle, WA (US)

(73) Assignee: Fred Hutchinson Research Center, Seattle, WA (US)

( * ) Notice: Subject to any disclaimer, the term of this patent is extended or adjusted under 35 U.S.C. 154(b) by 0 days.

(21) Appl. No.: 08/097,869

(22) Filed: Jul. 27, 1993

Related U.S. Application Data

(63) Continuation of application No. 07/753,178, filed on Aug. 30, 1991.

(51) Int. Cl.⁷ .................................................. C07K 14/00
(52) U.S. Cl. ............................................................ 530/351
(58) Field of Search ................................................ 530/351

(56) References Cited

U.S. PATENT DOCUMENTS 4,935,233 * 6/1990 Bell et al. ............................ 424/85.5

FOREIGN PATENT DOCUMENTS

WO9102754 * 3/1991 (WO) .

OTHER PUBLICATIONS

Williams & Park 1991. Hemato. Effects of a GMCS7/IL–3 Fusion Prot. Cancer 67: 2705.*
Simpson et al 1988. Struct. Char. of Mcerine Myeloid L17. Eur. J. Biochem. 175: 541.*
Yasukawa et al. 1987. Struct. & Expr. of heu–B Cell Shim Factor 2. EMBO J. 6(10): 2939.*
Malik et al. 1989. Mol. Clin. Seg. Anal. Funct. Exp. of Novel Gr. Reg. Oncostatin M. Molec. Cellul. Biol. 9(7): 2847.*
Bazan 1990 Immunology Today 11(10):350.*

* cited by examiner

*Primary Examiner*—Karen Cochrane Carlson
(74) *Attorney, Agent, or Firm*—Foley & Lardner

(57) ABSTRACT

Hybrid cytokines containing four helical regions, each of which is derived from a corresponding α-helical region in leukemia inhibitory factor (LIF), granulocyte colony stimulating factor (G-CSF), interleukin-6 (IL-6) or oncostatin-M (OSM) are disclosed. These hybrid cytokines may further contain linking regions also derived from corresponding linking regions in these factors. The hybrid cytokines offer a unique spectrum of activities useful in treating conditions for which the native cytokines are useful or in treating conditions characterized by an excess of the native cytokines.

16 Claims, 3 Drawing Sheets

FIG. 1B

```
hLIF     S L G N I T R D Q K I - - L N P S A L S L H S K L N A T A D I L R - - - - - - - - -
mLIF     S L T N I T R D Q K V - - L N P T A V S L Q V K L N A T I D V M R - - - - - - - - -
hOSM     T L - N A T L - G C V - - L H R L A D L E Q - R L P K A Q D L E R - S G L N I E D L
sOSM     T L - N D T L - G C V - - L H R L A D L E Q - H L P K A Q D L E R - S G L N I E D L
hG-CSF   A L - - - Q L A G C L S Q L H S G L F L Y Q - G L L - - Q A L E G I S P E L G P T L
mG-CSF   A L - - - Q Q T Q C L S Q L H S G L C L Y Q - G L L - - Q A L S G I S P A L A P T L
hiL-6    S G F N - - E E T C L V K I I T G L L E F E V Y L E Y L Q N R F E S S - - - E E Q A
miL-6    T G Y N - - Q F I C L L K I S S G L L E Y H S Y L E Y M K N N L K D N K - - K D K A hLIF     - - - - - - - - - - G L L S N V L C R - - - L C S K Y - - - - H V G H V D V - T Y
mLIF     - - - - - - - - - - G L L S N V L C R - - - L C N K Y - - - - R V G H V D V - P P
hOSM     E K L Q M A R P N I L G L R N N I Y C M A Q L L D N S D T A E P T K A G R G A S Q P P
sOSM     E K L Q M A R P N V L G L R N N I Y C M A Q L L D N S D M T E P T K A G R G A S Q P P
hG-CSF   D T L Q L - - - D V A D F A T T I W Q Q M E E L G M A P A L Q P T - - - Q G A - - - -
mG-CSF   D L L Q L - - - D V A N F A T T I W Q Q M E N L G V A P T V Q P T - - - Q S A - - - -
hiL-6    R A V Q M - - - S T K V L I Q F L Q K K A K N L D A I T T P I P T - - - T N A S L - -
miL-6    R V L Q R - - - D T E T L I H I F N Q E V K D L H K I V L P P I - - - S N A L L - - hLIF     G P D T S G K D V F Q K K K L G C Q L L G K Y K Q - I I A V L A Q A F
mLIF     V P D H S D K E A F Q R K K L G C Q L L G T Y K Q - V I S V V V Q A F
hOSM     T P T P A - S D A F Q R K L E G C R F L H G Y H R - F M H S V G R V F S K W G E S P N R
sOSM     T P T P T - S D V F Q R K L E G C S F L H G Y H R - F M H S V G Q V F S K W G E S P N R
hG-CSF   - - M P A F A S A F Q R R A G G V - L V A S H L Q S F L E V S Y R V L R H L A Q P
mG-CSF   - - M P A F T S A F Q R R A G G V - L A I S Y L Q G F L E T A R L A L H H L A
hiL-6    L T K L Q A Q N Q W L Q D M T T H L I L R S F K E - F L Q S S L R A L R Q M
miL-6    T D K L E S Q K E W L R T K T I Q F I L K S L E E - F L K V T L R S T R Q T hOSM     S R R / H S P H Q A L R K G V R R T R P S R K G K R L M T R G Q L P R
sOSM     S R R / H S P H Q A L R K G V R R T R D S R K G N R L M T R G Q L . .
```

HYBRID CYTOKINES

This application is a Continuation of application Ser. No. 07/753,178, filed Aug. 30, 1991.

TECHNICAL FIELD

The invention relates to the field of cell proliferation and differentiation and to factors which regulate the composition of the blood and the viability of other tissues. More specifically, the invention concerns hybrid cytokines which have unique physiological properties derived from the cytokine family members leukemia inhibitory factor (LIF); granulocyte colony stimulating factor (G-CSF); interleukin-6 (IL-6); and oncostatin-M (OSM).

BACKGROUND ART

More than two dozen cytokines that regulate blood composition by controlling the growth and differentiation of hematopoietic stem cells have been identified. The interferons, tumor necrosis factor, stem cell factor, the numbered interleukins and the various colony stimulating factors are exemplary of these proteins and glycoproteins. The invention described below focuses on four closely related cytokines whose structural similarity has been discovered by applicants.

One of these factors, interleukin-6 (IL-6) was originally identified as a B-cell differentiation factor, but has subsequently been shown to induce acute phase proteins in liver cells, to inhibit growth of certain myeloid leukemia cell lines and induce their differentiation into macrophage cells, to promote IL-3 dependent colony formation of primitive blast colony forming cells, to cause differentiation of neuronal cells, to enhance keratinocyte and mesangial cell growth, to promote the maturation of megakaryocytes, and to induce the proliferation and differentiation of T cells. In vivo, IL-6 increases the hematopoietic cell count of the erythroid, myeloid, and thrombocytic lineages. Other former names for IL-6 are beta2-interferon, B-cell stimulatory factor-2, hybridoma/plasmacytoma growth factor, and monocyte granulocyte inducer type 2. The spectrum of activities attributable to IL-6 indicates that it is useful in tumor inhibition, bone remodeling, kidney development, and T- and B-cell proliferation and stimulation.

Leukemia inhibitory factor (LIF) has been demonstrated to inhibit the growth of certain myeloid leukemia cells and to induce their differentiation into macrophage cells; to enhance interleukin-3 dependent colony formation of primitive blast cells; to promote megakaryocyte growth and differentiation; to induce neuronal differentiation; to stimulate the production of acute phase proteins and hepatocytes (all properties it shares with IL-6) and to inhibit the differentiation of embryonic stem cells and kidney cells and to induce bone resorption.

Oncostatin-M (OSM) is known to be a tumor inhibitor for melanoma and certain carcinoma cells and inhibits the growth of human A375 melanoma cells but not normal human fibroblasts. It is also an inhibitor of the growth of M1 myeloid leukemic cells and induces their differentiation into macrophage-like cells as well as stimulating megakaryocyte production in the spleen. This factor was first isolated from conditioned medium of U937 human histolytic leukemia cells that had been induced with phorbol myristate acetate (PMA) and is also present in the supernatants of activated human T-cells.

Granulocyte colony stimulating factor (G-CSF) stimulates neutrophil proliferation and differentiation and induces the differentiation of M1 murine myeloid leukemic cells into macrophage-like cells as well as enhancing interleukin-3 dependent colony formation of primitive blast cells. It appears to have little effect on the hematopoietic cell lineages of megakaryocytes or platelets but enhances cytosine arabinoside-mediated cytoxicity in human myeloid leukemia cells.

The reported biological activities of the foregoing cytokine family members is summarized in the following table:

TABLE 1

| Reported Biological Activities of Cytokine Family Members | | | | |
|---|---|---|---|---|
| | LIF | OSM | G-CSF | IL-6 |
| Endothelial Cell Proliferation | NR | + | NR | NR |
| Tumor Inhibition | + | + | NR | + |
| Embryonic Stem Cell Maintenance | + | + | NR | NR |
| Hematopoietic Leukemic Cell Differentiation | + | + | + | + |
| Melanoma Cell Inhibition | − | + | − | + |
| Neutrophil Proliferation/Stimulation | NR | NR | + | + |
| Myoblast Proliferation | + | NR | NR | NR |
| Bone Remodeling | + | NR | NR | + |
| Kidney Development | + | NR | NR | NR |
| Neuronal Differentiation | + | NR | NR | + |
| Hepatocyte Stimulation | + | NR | NR | + |
| Megakaryocyte Augmentation | + | NR | − | + |
| T-Cell Proliferation | NR | NR | NR | + |
| Keratinocyte Proliferation | NR | NR | NR | + |
| B-Cell Proliferation/Stimulation | NR | NR | NR | + |
| Binding to Human Placental Cell Receptor | + | + | − | − |

These data were obtained from multiple assay systems and few direct comparisons of the growth factors have been made. The table lists several biological systems in which one of the four growth factors shows activity, while the role of other family members is not yet known. NR = not reported.

As shown in the foregoing table, the four related factors that are the subject of the present invention do not display identical activity patterns. Although a number of characteristics have not yet been reported for each of these factors, it is clear that at least one difference in activity spectrum exists between any two of them. For example, OSM and IL-6 inhibit the growth of melanoma cells; LIF and G-CSF do not. However, LIF and G-CSF differ in that LIF is capable of augmenting megakaryocytes; G-CSF is not. OSM binds to human placental cell receptor; IL-6 does not.

While there have been excellent clinical successes, especially with the use of G-CSF in enhancing the health of the immune system and white blood cell replacement in patients with depleted lymphocyte populations, such as patients undergoing radiation or chemotherapy, no ideal pharmaceutical which has the desired effects, free of complications, has been discovered. Clearly this is not surprising, since normally the composition of the blood is regulated by controlling the differentiation of cells originating in the bone marrow through the interaction of a multiplicity of indigenous factors whose levels are in turn presumably controlled by mechanisms not yet understood. Thus, it is desirable to augment the repertoire of available therapeutic agents which participate in the control of blood composition. The present invention augments this repertoire by providing hybrid cytokines with unique properties characteristic of these previously unavailable therapeutic agents.

DISCLOSURE OF THE INVENTION

The invention is directed to therapeutic hybrid cytokines which are composed of portions of the closely related cytokines leukemia inhibitory factor (LIF), granulocyte-colony stimulating factor (G-CSF), interleukin-6 (IL-6) and oncostatin-M (OSM). These cytokines have a high degree of sequence homology (as well as a similar genetic organization. It is disclosed in the art that IL-6 and G-CSF are comprised of four α-helical regions; applicants herein have deduced that LIF and OSM also are comprised of four α-helical regions organized in a similar manner. In each case, the four helical regions are linked by non-α helical sequences of about 5–100 amino acids, and in some cases the α-helices are maintained in the proper conformation and geometry with respect to each other through disulfide bridges. The hybrid cytokines of the invention also contain four α-helical regions, at least two of which are derived from the corresponding α-helical regions of different members of this group. The linking amino acid sequences preferably are also derived from the four factors described herein.

Thus, in one aspect, the invention is directed to a hybrid cytokine comprising a first, second, third and fourth α-helical region. Each of these regions is derived from the corresponding α-helical region of LIF, G-CSF, IL-6, or OSM. At least one of these regions is derived from a different factor of this group than at least one other.

In additional aspects, the invention is directed to DNA sequences encoding the hybrid cytokines, to expression systems capable of expressing these DNAs, to host cells transformed with these expression systems and to methods to produce the hybrid cytokines recombinantly. In still other aspects, the invention is directed to pharmaceutical compositions containing the hybrid cytokines of the inventions and to methods to effect therapies using these compositions. In addition, the invention is directed to antibodies or fragments specifically immunoreactive with these hybrid cytokines.

BRIEF DESCRIPTION OF THE DRAWINGS

FIGS. 1A and 1B show the complete amino acid sequences of LIF, OSM, G-CSF and IL-6 from various species—human, murine, and simian. (SEQ ID NO:1), (SEQ ID NO:2), (SEQ ID NO:3), (SEQ ID NO:4), (SEQ ID NO:5), (SEQ ID NO:6), (SEQ ID NO:7), and (SEQ ID NO:8).

MODES OF CARRYING OUT THE INVENTION

Figure 1A:
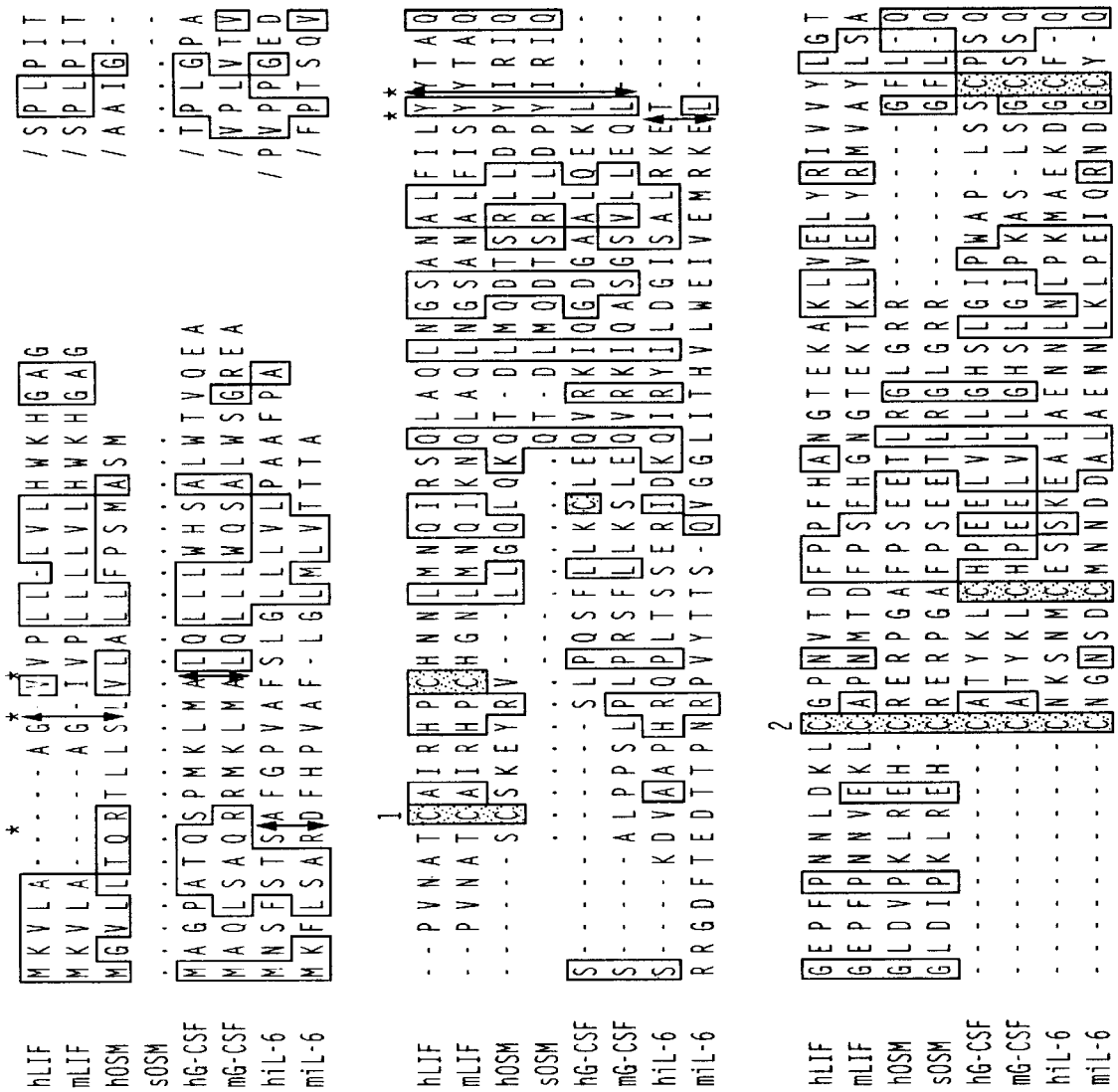

The availability of the DNA sequences encoding the four factors used as portions of the hybrid, LIF, G-CSF, IL-6 and OSM, makes possible the construction of recombinant DNA encoding the desired hybrid cytokine. As shown in FIG. 1, the complete amino acid sequence (and corresponding DNA sequence) is available with respect to human, murine and simian forms of these cytokines. The close homology shown among species also makes possible the retrieval of the corresponding DNAs from additional species producing such cytokines, such as feline, canine, bovine, avian, and other vertebrate species. Natural allelic variants may also be retrieved. Accordingly, the hybrid cytokine encoding DNA can be constructed using DNAs of species origin appropriate for the particular hybrid desired.

The DNA encoding the amino acid sequences of the hybrid cytokines will be "derived from" the DNA encoding the relevant portions of the native cytokine. By "derived from" is meant that the amino acid sequence encoded is the same as that of the native protein—either that shown in FIG. 1, a naturally-occurring allelic variant, a mutant shown to bind to the receptor of the relevant cytokine in standard in vitro assays, or that of an additional species obtainable by using the known species DNA as probes. "Derived from" does not imply any physical derivation. Typically, the portions of the protein sequence "derived from" the native cytokines are, in fact, prepared using either genomic or cDNA, synthesized DNA, or combinations of these. Of course, any DNA encoding the desired sequence can be used, not necessarily that DNA sequence which occurs natively. "Derived from," thus, has no implications that the physical embodiment of either the DNA or the protein portion is used in the hybrids of the invention, but that the information provided by the native sequences is used in the construction of suitable DNA and protein.

Exemplary amino acid sequences for the relevant cytokines of various species are shown in FIG. 1. The hybrid cytokines of the invention derive amino acid sequences from at least two of the four related factors—leukemia inhibitory factor (LIF), granulocyte-colony stimulating factor (G-CSF), interleukin-6 (IL-6), and oncostatin-M (OSM). The amino acid sequences of each of these factors in human and other species is known, and the encoding genes have been cloned. Human and murine genes encoding LIF are reported by Moreau, J. F., et al., *Nature* (1988) 336:690–692; and by Simpson, R. J., et al., *Eur J Biochem* (1988) 175:541–547; for human and murine G-CSF by Nagata, S., et al., *Embo J* (1986) 5:575–581, and by Tsuchiya, M., et al., *Proc Natl Acad Sci USA* (1986) 83:7633–7637; for human and murine IL-6 by Yasukawa, K., et al., *Embo J* (1987) 6:2939–2945, and by Tanabe, O., et al., *J Immunol* (1988) 141:3875–3881; and for human OSM by Malik, N., et al., *Mol Cell Biol* (1989) 9:2847–2853; and for simian OSM (unpublished results).

Alignments for the amino acid sequences of these proteins are shown in FIG. 1. The homology correlations, alignment, and secondary structure determinations were conducted using a number of software packages including PatMat software (Henikoff, S., et al., *Methods Enzymol* (1990) 183:111–132; GenPro software (Riverside Scientific, Seattle, Wash.)); P/C Gene Software, Intelligenetics, Inc. (Mountain View, Calif.); Scor Edit from J. Durand (Seattle, Wash.); Motif Program (Smith, H. O., *Proc Natl Acad Sci USA* (1990) 87:826–830) as implemented in the Protomat/Motif J software from S. Henikoff (Seattle, Wash.).

Application and interpretation of these programs also led to a prediction of secondary structure for the four factors which comprise the cytokines of the invention.

Figure 2:
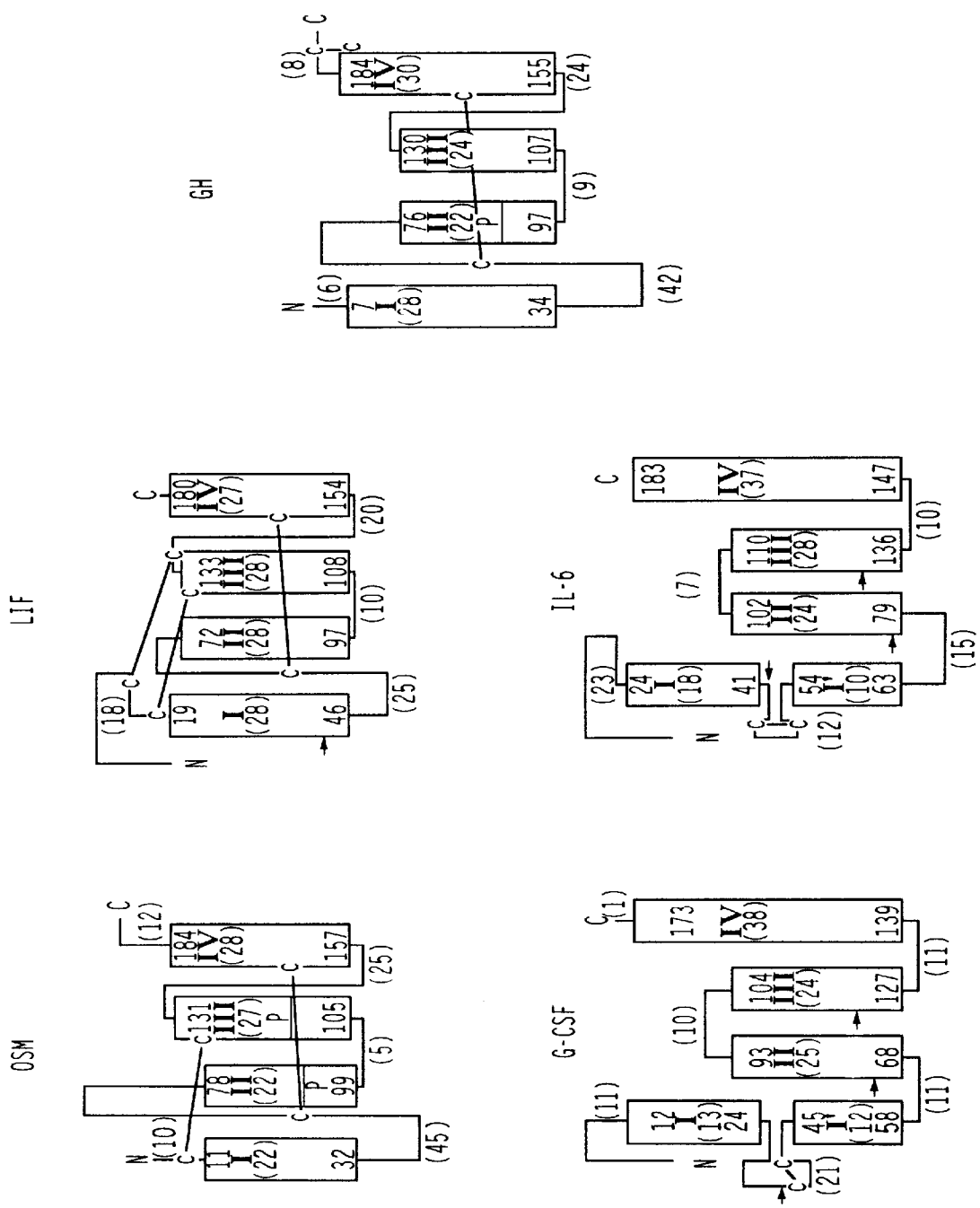
FIG. 2 shows the three-dimensional organization deduced for the OSM, LIF, G-CSF and IL-6 factors used to construct the hybrids of the invention. Also shown in this figure is the three-dimensional organization of growth hormone which has been confirmed by X-ray crystallography.

The results of this work are shown in FIG. 2. As shown in FIG. 2, each of LIF, G-CSF, IL-6, and OSM contain four α-helical regions numbered I–IV. The various factors also show disulfide bridges; OSM and LIF having similar locations for the disulfides; as shown OSM and LIF show similar genetic patterns; G-CSF and IL-6 also show similar patterns with each other. The disulfide bond linking the fourth α-helical region and the linking region between the first and second α-helices predicted in LIF and shown to be present in OSM is also found in the structure of growth hormone.

In human OSM, the α-helical region I extends approximately from amino acid 11–32; α-helical region II from 78–99; α-helical region III from 105–131; and α-helical region IV from 157–184. The locations of the various regions of α-helices for the human forms in these four factors are shown in Table 2.

TABLE 2

| Factor | Region | | | |
| --- | --- | --- | --- | --- |
| | I | II | III | IV |
| OSM | 11–32 | 78–99 | 105–131 | 157–184 |
| LIF | 19–46 | 72–97 | 108–133 | 154–180 |
| G-CSF | 12–24, 45–56 | 68–93 | 104–127 | 139–173 |
| IL-6 | 24–41, 54–63 | 79–102 | 110–136 | 147–183 |

As implied in the table, the various helical regions in each case will be linked by nonhelical peptide sequences designated herein "linking sequences." Thus, for OSM, for example, linking sequence I/II extends from residue 33–77; linking region II/III from position 100–104; and linking region III/IV from position 132–156. In G-CSF and IL-6, the α-helical region I is divided into two portions separated by a nonhelical portion in each case. As shown, some of the linking regions, such as OSM linking region II/III are quite short—in this case, only about 5 amino acids. In other cases, an extended linking region is found.

The hybrid cytokines of the invention contain four helical regions each derived from the "corresponding" helical region in one of the four factors described above. As used herein, derived from the "corresponding" α-helical region means that the first α-helical region (I) of the hybrid cytokine contains the same or substantially identical amino acid sequence as α-helical region I of either OSM, LIF, G-CSF or IL-6; the second α-helical region (II) of the hybrid cytokine has the same or substantially identical amino acid sequence as that of α-helical region II of one of these factors, and so forth. The four α-helical regions of the hybrid cytokines are connected by additional nonhelical linking regions ranging from about 4 to about 100 amino acids. In addition, each of the helical regions may be interrupted by one or more nonhelical sequences containing about 8–30 amino acids, analogous to the situation for the first helical regions of the native forms of G-CSF and IL-6.

It is preferred that the helical regions in the hybrid be derived from the cytokine characteristic of the species for which the use is intended. Thus, for human therapy, it is preferred that all four of the regions be derived from the human forms of the cytokines. For veterinary use, for example, in dogs, it is preferred that all of the helical regions derive from the dog corresponding regions. However, in view of the homology exhibited among species with respect to these cytokines, it is within the scope of the invention to combine regions derived from various species.

It is also preferred that the nonhelical linking regions be derived from the corresponding linking regions in the native cytokines. Thus, it is preferred that linking region I/II in the hybrid be derived from linking region I/II of one of the G-CSF, OSM, LIF and IL-6. Derivation from the species for which use is intended is also preferred. However, included within the scope of the invention are hybrid molecules which have arbitrarily chosen linking regions selected to keep the conformation of the three-dimensional molecules similar to those of the native cytokines.

In preferred embodiments, either helical regions I, II, and III are derived from the same factor and IV from a different factor or, conversely, regions II, III and IV are from the same factor and region I is from a different one. In general, it is preferred that regions II and III derive from the same source.

Also preferred are embodiments wherein the relative polarity orientation of regions I–IV is undisturbed from a natural pattern, in particular, regions I and IV with respect to each other. It will be noted that in all four factors the N→C directions of regions I and IV are opposite. Similarly, the N→C orientations of regions II and III are of opposite polarity. In OSM and LIF, the lengths of the linking region I/II and of linking region III/IV permit regions I and IV to be oriented N→C in the same orientation as regions II and III, respectively. The short segments in the linking regions I/II and III/IV in G-CSF and IL-6 force regions I and II and III and IV to be in opposite orientations N→C, respectively. However, the "double negative" for G-CSF and IL-6 results in the same relative orientations with respect to regions I and IV in G-CSF and IL-6 as is the case in OSM and LIF.

Thus, in preferred embodiments, either both of linking regions I/II and III/IV will be of about 20–100 amino acids to allow for the parallel orientation of joined helical regions as in LIF and OSM, or both should be relatively short of less than 20 amino acids to force antiparallel orientation in both cases as in G-CSF and IL-6. Thus, the linking regions should be selected so as to assure antiparallel orientation of regions I and IV in all cases.

Also particularly preferred embodiments are those wherein the first and second α-helical regions are derived from G-CSF or wherein at least one region is derived from IL-6. Particularly preferred embodiments with respect to the origin of the α-helical regions are as follows, wherein the α-helical regions I–IV are ordered as shown, and wherein G represents G-CSF; L represents LIF; I represents IL-6; and O represents OSM: GGGI; OOOI; LLLI; IIIO; GGGO; OOOG; LLLO; IIIG; GGGL; OOOL; LLLG; IIIL; IGGG; IOOO; ILLL; OIII; OGGG; GOOO; OLLL; GIII; LGGG; LOOO; GLLL; LIII; GGLL; GGII; GGOO; GILO; LOGI; LLII; LLGG; IIGG; and OOGG.

The α-helical regions shown are, then, linked through nonhelical linking regions of 4–100 amino acids, preferably derived from the linking regions of the native cytokines. Thus, preferred embodiments of the foregoing are those wherein the linking regions are as indicated derived from the corresponding linking region of the native cytokine. In the abbreviations used in the following, g represents a linking region from G-CSF; l represents a linking region from LIF; i represents a linking region from IL-6; and o represents a linking region from OSM. In each case, the indicated linking region is derived from the corresponding linking region of the indicated cytokine; thus that shown between α-helical sequence I and II is derived from the linking region I/II.

Thus, especially preferred are the following: GlGiLiL; GlGgIlI; GgGgOgO; GlGiGoI; IiGgGgG; GgIiLiO; LgOgGgI; LoLlIoI; GgGgGgO; GgGgGgL; OoOoOoG; LlLlLlG; GoOoOoO; OgGgGgG; LgGgGgG; GiGgGil.

As it is believed that the disulfide linkages shown in FIG. 2 are helpful in maintaining conformation, choice of the suitable linking region or α helical region which provides cysteine residues to furnish the appropriate disulfide links are preferred. Alternatively, 4 cysteine residue may be substituted at the appropriate position in place of one of the residues in the linking or helical region derived from a different source.

Synthesis of the Hybrid Cytokines

The hybrid cytokines, in principle, could be made using standard solid-phase peptide synthesis techniques, in combination with linking technology. However, synthesis of peptides of the appropriate length is laborious and difficult. Conditions would need to be provided subsequent to the synthesis to effect the three-dimensional folding required for the molecules to assume the α-helical and tertiary conformations shown. A more practical approach to the preparation of the hybrid cytokines of the invention is the recombinant production thereof.

Use of recombinant technology to produce any desired protein is by now well established in the art. The requirements for such recombinant production are well known—the provision of a coding sequence for the desired protein, which coding sequence will be operably linked to additional DNA sequences capable of effecting its expression. It may be desirable to produce the hybrid cytokines as fusion proteins which can be freed from upstream or downstream (or intermediate) regions or to produce them linked to leader sequences capable of effecting the secretion of the desired cytokines into the cell culture medium.

The DNA-based expression system will also contain "control sequences" which are necessary for the transcription and translation of the message. Known components required for expression include promoter systems which may be constitutive or inducible, translational initiation signals, in eucaryotic expression, polyadenylation translation termination sites, and transcription terminating sequences. Host vectors containing these controls which permit desired coding sequences to be operably linked to the required control systems are by now well established in the art, and such vectors operable in a variety of hosts can be found.

Thus, the hybrid cytokines of the invention may be produced in procaryotic cells using appropriate controls, such as the trp or lac promoter, or in eucaryotic host cells which are capable of effecting the post-translational processing that permits that protein to assume the desired three-dimensional conformation. Eucaryotic control systems and host vectors are also well known; including the leu and glycolytic promoters useful in yeast, the viral SV40 and adenovirus promoters in mammalian cells, inducible promoters such as the metallothionein promoter also suitable for mammalian cells, and the baculovirus system which is operable in insect cells. Plant vectors with suitable promoters, such as the nos promoter are also well known.

The hybrid cytokines of the invention can be prepared conveniently in procaryotic as well as eucaryotic hosts since, although generally glycosylated in their native forms, glycosylation is known not to be essential for their activity. Suitable conditions for refolding can also be provided as is understood in the art.

Standard techniques for expression of DNAs encoding any desired protein and techniques and methodologies for culturing the appropriate cells, providing the conditions suitable for expression, and recovering the protein from the culture are summarized, for example, in standard laboratory manuals, such as those published by Cold Spring Harbor Laboratories, Cold Spring Harbor, N.Y.

Thus, for recombinant production of the hybrid cytokines, suitably constructed DNA encoding the desired hybrid is operably linked to control sequences in a suitable expression system which is then transformed or transfected into a compatible host. The host cells are cultured using conditions appropriate to their growth, and expression is preferably induced after some growth has occurred. Production of the hybrid cytokine is then monitored and the cytokine collected from the culture either from the supernatant or by lysing the cells.

Purification procedures analogous to those known in the art for the native cytokines can be used to effect purification of the cytokine to a form suitable for therapeutic or diagnostic use.

Preparation of Antibodies

Antibodies specifically reactive with the hybrid cytokines of the invention or immunoreactive fragments of these antibodies may be prepared using standard immunization protocols. These may be utilized as polyclonal antisera or the spleen cells or peripheral blood lymphocytes of the immunized animals may be immortalized to obtain isolated cell cultures which produce monoclonal antibodies specific for these hybrids. The antibodies may be used intact, or as fragments such as Fab, Fab' or F(ab')$_2$ fragments. As the hybrid cytokines are relatively large proteins, it should not be necessary to enhance their immunogenicity by conjugation to carrier; however, such enhancement is possible and construction of such conjugates is well known in the art.

Thus, the hybrid cytokine, optionally conjugated to an immunological carrier, is administered in a standard immunization protocol with or without the use of adjuvant to a suitable subject, usually rats, sheep, or rabbits. Antibody formation is monitored by titrating the serum using the cytokine as antigen and employing standard immunoassay techniques. When high titers are achieved, the sera can be used per se or the spleen cells or peripheral blood lymphocytes isolated and immortalized, for example, using the fusion technique of Kohler and Millstein to provide immortalized cells capable of secreting the desired monoclonal antibodies. Individual clones of these immortalized cells are then screened, again using standard immunological techniques, for those colonies which secrete antibodies specifically immunoreactive with the hybrid cytokine immunogen.

The antibodies prepared in the foregoing manner or fragments thereof are useful in diagnostic assays for monitoring the pharmacokinetics and progress of therapeutic regimens using the hybrid cytokines of the invention. Thus, the dosage levels of the hybrid cytokines in the therapeutic applications set forth below can be regulated according to the metabolic fate of the previously administered dosages.

Administration and Utility

The hybrid cytokines of the invention are useful in treating the indications for which their native counterparts are often employed. However, the hybrid forms of the cytokines possess unique properties which make them suitable alternatives in the methods and procedures commonly employed with respect to the native molecules.

In addition, some of the hybrid cytokines are capable of binding the receptors ordinarily bound by the native molecules but fail to activate these receptors. These forms of the hybrid cytokines are, thus, antagonists. These may be useful in treating conditions where presence of the parent factor that ordinarily binds to the receptor is responsible for undesired cell proliferation. For example, IL-6 and OSM are known to be associated in high levels with Kaposi's sarcoma. These are found also in high concentrations in the synovial fluid from patients suffering from rheumatoid arthritis. In these conditions, the hybrid cytokine antagonists are particularly useful.

Conversely, the hybrid cytokines which are agonists can be employed in circumstances wherein the native cytokines are often used. For instance, these agonist hybrid cytokines may be used in liver cell regeneration and in in vitro fertilization procedures to enhance these processes.

The hybrid cytokine may possess properties exhibited by neither of its components taken alone. It is known, for example, that coadministration of LIF and G-CSF results in a synergistic effect in inhibiting colony formation and inducing differentiation of human U937 and HL60 myelocytic leukemia cell lines although neither alone has this effect (Maekawa, T., and Metcalf, D., *Leukemia* (1989) 3:270–276.) Similarly, applicants have found that although neither LIF nor OSM inhibit colony formation of U937, when supplied in combination, at 10 ng/ml using 300 cells in soft agar, more than 60% inhibition of colony formation is obtained.

Thus, combination of the α-helical regions from more than one growth factor results in hybrid cytokines with a unique spectrum of properties. These hybrid cytokines are useful generally in inhibiting tumor proliferation, in bone remodeling, in stimulating the growth of desired cells, such as neurites or T-cells, and in enhancing the differentiation of hematopoietic cells. These factors are therefore highly useful in the direct treatment in the malignancies. They are especially useful in maintaining the general health and immune capacity of a subject undergoing radiation therapy or chemotherapy for such indications.

The selection of particular conditions or procedures suitable for the hybrid cytokine in question depends, of course, on its particular spectrum of agonist or antagonist activities.

The properties of a particular hybrid can be ascertained through standard in vitro tests well known in the art. Such tests include those, for example, which show induction of differentiation into macrophages (Tomita, M., et al., *J Biol Chem* (1984) 259:10978–10982); ability to enhance interleukin-3-dependent colony formation of primitive blast cells (Leary, A. G., et al., Blood (1990) 75:1960–1964); promotion of megakaryocyte growth and differentiation (Metcalf, D., et al., *Blood* (1990) 76:50–56); induction of neuronal differentiation (Yamamuri, T., et al., *Science* (1989) 246:1412–1416); and induction of bone resorption (Ishimi, Y., et al., *J Immunol* (1990) 145:3297–3303). A large number of indicators in vitro of the ability of these factors to stimulate growth and differentiation of desired cells and inhibit the growth of undesired malignant cells is known in the art. Animal model systems can also be used to verify the unique spectrum of properties associated with each hybrid cytokine.

Particularly useful in vitro tests which can be used to confirm the spectrum of activity of the hybrid cytokines are as follows:

The inhibition of DNA synthesis in M-1 myeloid leukemic cells can be measured; the effect on growth of human A-375 melanoma cells (Zarling, J. M. et al., *Proc Natl Acad Sci USA* (1986) 83:9739–9743) may be measured, or the effect of these factors on embryonic stem cells cultured in vitro as described by Smith, A. G. et al., *Devel Biol* (1987) 121:1–9; Williams, R. L. et al., *Nature* (1988) 336:684–687, can be determined.

The foregoing procedures can be adapted to assess both agonist and antagonist behavior. In assessing antagonist behavior, the candidate hybrid cytokine is used in the presence of a known agonist and its effect on the activity of the known agonist is assessed.

As set forth above, the hybrid cytokines of the invention are applicable to in vivo and in vitro procedures involving both human and animal cells. They are suitable for both medical and veterinary use.

For therapeutic use, the hybrid cytokines of the invention are formulated into standard pharmaceutical compositions suitable for the administration of proteins. Suitable formulations can be found, for example, in *Remington's Pharmaceutical Sciences*, latest edition, Mack Publishing Company, Easton, Pa. Comparable compositions for veterinary use are also known in the art. Generally, administration is systemic, usually by injection, such as intravenous or intramuscular injection or can be effected by transdermal or preferably transmucosal delivery. Suitable formulations for effecting transmucosal delivery include, for example, various detergents and bile salts or fusidic acid derivatives. Enteric compositions which permit oral administration may also be employed.

The dosage levels of the hybrid cytokines of the invention are comparable to those useful for the native molecules. These levels are understood in the art, and the precise dosage can be adjusted according to the condition of the patient, the mode of administration, and the judgment of the attending physician.

The hybrid cytokines of the invention may also be labeled using suitable fluorometric, colorimetric, enzymic, or radioactive labels for use in assays to ascertain the formation of antibodies in patients being treated.

What is claimed is:

1. A hybrid cytokine comprising a first, second, third and fourth α-helical region wherein each of said first, second, third and fourth α-helical regions is derived from the corresponding α-helical region of a factor selected from the group consisting of leukemia inhibitory factor (LIF or L), granulocyte-colony stimulating factor (G-CSF or G), interleukin-6 (IL-6 or I), and oncostatin-M (OSM or O); and wherein at least one said α-helical region of said cytokine is derived from a factor different from that from which at least one additional region of said cytokine is derived.

2. The hybrid cytokine of claim 1 wherein said first and second α-helical regions are derived from G-CSF.

3. The hybrid cytokine of claim 2 which is selected from the group consisting of GGLL, GGII and GGOO.

4. The hybrid cytokine of claim 1 which is selected from the group consisting of GILO, LOGI, LLGG; IIGG; OOGG; and LLII.

5. The hybrid cytokine of claim 1 wherein three consecutive α-helical regions are derived from the same factor.

6. The hybrid cytokine of claim 5 which is selected from the group consisting of GGGI; OOOI; LLLI; IIIO; GGGO; OOOG; LLLO; IIIG; GGGL; OOOL; LLLG; IIIL; IGGG; IOOO; ILLL; OIII; OGGG; and GOOO.

7. The hybrid cytokine of claim 1 which further contains, between each of said first, second, third and fourth α-helical regions linking regions of 5–100 amino acids.

8. The cytokine of claim 7 wherein each of said linking regions is independently derived from a corresponding linking region of LIF, G-CSF, IL-6 or OSM.

9. The hybrid cytokine of claim 7 wherein each of said linking regions between said first and second, and between said third and fourth α-helical region is selected so as to result in an anti-polar orientation of said first and fourth α-helical region.

10. The hybrid cytokine of claim 9 wherein the linking regions between said first and second and said third and fourth α-helical regions are each 20–100 amino acids.

11. The hybrid cytokine of claim 9 wherein each of the linking regions between said first and second and said third and fourth α-helical regions are each less than 20 amino acids.

12. The hybrid cytokine of claim 9 wherein each of said linking regions between said first and second and said third and fourth α-helical regions are either both derived from OSM and/or LIF or both derived from G-CSF and/or IL-6.

13. The cytokine of claim 9 which is selected from the group consisting of GlGlLlL; GlGgIll; GgGgOgO; GlGiGoI; IiGgGgG; GgIiLiO; LgOgGgI; GgGgGgO; GgGgGgL; OoOoOoG; LlLlLlG; GoOoOoO; OgGgGgG; LgGgGgG; GiGgGiI; and LoLlIoI.

14. The cytokine of claim 1 wherein each said corresponding region is human.

15. The hybrid cytokine of claim 1 conjugated to label.

16. A pharmaceutical or veterinary composition useful in affecting the proliferation and/or differentiation of target cells which composition comprises an effective amount of the hybrid cytokine of claim 1 in admixture with at least one pharmaceutically acceptable excipient.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 202 amino acids
      (B) TYPE: amino acid
      (C) STRANDEDNESS: single
      (D) TOPOLOGY: linear (xi) SEQUENCE DESCRIPTION: SEQ ID NO:1:

```
Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45
```

```
Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
                115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Lys Leu Gly Cys Gln Leu Leu Gly Lys Tyr Lys
            180                 185                 190

Gln Ile Ile Ala Val Leu Ala Gln Ala Phe
            195                 200

(2) INFORMATION FOR SEQ ID NO:2:

(i) SEQUENCE CHARACTERISTICS:
        (A) LENGTH: 203 amino acids
        (B) TYPE: amino acid
        (C) STRANDEDNESS: single
        (D) TOPOLOGY: linear (xi) SEQUENCE DESCRIPTION: SEQ ID NO:2:

Met Lys Val Leu Ala Ala Gly Ile Val Pro Leu Leu Leu Leu Val Leu
1               5                   10                  15

His Trp Lys His Gly Ala Gly Ser Pro Leu Pro Ile Thr Pro Val Asn
                20                  25                  30

Ala Thr Cys Ala Ile Arg His Pro Cys His Gly Asn Leu Met Asn Gln
            35                  40                  45

Ile Lys Asn Gln Leu Ala Gln Leu Asn Gly Ser Ala Asn Ala Leu Phe
    50                  55                  60

Ile Ser Tyr Tyr Thr Ala Gln Gly Glu Pro Phe Pro Asn Asn Val Glu
65                  70                  75                  80

Lys Leu Cys Ala Pro Asn Met Thr Asp Phe Pro Ser Phe His Gly Asn
                85                  90                  95

Gly Thr Glu Lys Thr Lys Leu Val Glu Leu Tyr Arg Met Val Ala Tyr
            100                 105                 110

Leu Ser Ala Ser Leu Thr Asn Ile Thr Arg Asp Gln Lys Val Leu Asn
            115                 120                 125

Pro Thr Ala Val Ser Leu Gln Val Lys Leu Asn Ala Thr Ile Asp Val
    130                 135                 140

Met Arg Gly Leu Leu Ser Asn Val Leu Cys Arg Leu Cys Asn Lys Tyr
145                 150                 155                 160

Arg Val Gly His Val Asp Val Pro Pro Val Pro Asp His Ser Asp Lys
                165                 170                 175

Glu Ala Phe Gln Arg Lys Lys Leu Gly Cys Gln Leu Leu Gly Thr Tyr
            180                 185                 190

Lys Gln Val Ile Ser Val Val Val Gln Ala Phe
            195                 200
```

(2) INFORMATION FOR SEQ ID NO:3:

(i) SEQUENCE CHARACTERISTICS:
        (A) LENGTH: 252 amino acids
        (B) TYPE: amino acid
        (C) STRANDEDNESS: single
        (D) TOPOLOGY: linear (xi) SEQUENCE DESCRIPTION: SEQ ID NO:3:

```
Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
        35                  40                  45

Met Gln Asp Thr Ser Arg Leu Leu Asp Pro Tyr Ile Arg Ile Gln Gly
    50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
    130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
        195                 200                 205

Phe Ser Lys Trp Gly Glu Ser Pro Asn Arg Ser Arg Arg His Ser Pro
    210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
                245                 250
```

(2) INFORMATION FOR SEQ ID NO:4:

(i) SEQUENCE CHARACTERISTICS:
        (A) LENGTH: 206 amino acids
        (B) TYPE: amino acid
        (C) STRANDEDNESS: single
        (D) TOPOLOGY: linear (xi) SEQUENCE DESCRIPTION: SEQ ID NO:4:

```
Gln Thr Asp Leu Met Gln Asp Thr Ser Arg Leu Leu Asp Pro Tyr Ile
1               5                   10                  15

Arg Ile Gln Gly Leu Asp Ile Pro Lys Leu Arg Glu His Cys Arg Glu
            20                  25                  30

Arg Pro Gly Ala Phe Pro Ser Glu Glu Thr Leu Arg Gly Leu Gly Arg
        35                  40                  45
```

```
Arg Gly Phe Leu Gln Thr Leu Asn Asp Thr Leu Gly Cys Val Leu His
        50                  55                  60

Arg Leu Ala Asp Leu Glu Gln His Leu Pro Lys Ala Gln Asp Leu Glu
 65                  70                  75                  80

Arg Ser Gly Leu Asn Ile Glu Asp Leu Glu Lys Leu Gln Met Ala Arg
                 85                  90                  95

Pro Asn Val Leu Gly Leu Arg Asn Asn Ile Tyr Cys Met Ala Gln Leu
            100                 105                 110

Leu Asp Asn Ser Asp Met Thr Glu Pro Thr Lys Ala Gly Arg Gly Ala
            115                 120                 125

Ser Gln Pro Pro Thr Pro Thr Pro Thr Ser Asp Val Phe Gln Arg Lys
            130                 135                 140

Leu Glu Gly Cys Ser Phe Leu His Gly Tyr His Arg Phe Met His Ser
145                 150                 155                 160

Val Gly Gln Val Phe Ser Lys Trp Gly Glu Ser Pro Asn Arg Ser Arg
                165                 170                 175

Arg His Ser Pro His Gln Ala Leu Arg Lys Gly Val Arg Arg Thr Arg
            180                 185                 190

Pro Ser Arg Lys Gly Asn Arg Leu Met Thr Arg Gly Gln Leu
            195                 200                 205

(2) INFORMATION FOR SEQ ID NO:5:

(i) SEQUENCE CHARACTERISTICS:
        (A) LENGTH: 204 amino acids
        (B) TYPE: amino acid
        (C) STRANDEDNESS: single
        (D) TOPOLOGY: linear (xi) SEQUENCE DESCRIPTION: SEQ ID NO:5:

Met Ala Gly Pro Ala Thr Gln Ser Pro Met Lys Leu Met Ala Leu Gln
 1               5                  10                  15

Leu Leu Leu Trp His Ser Ala Leu Trp Thr Val Gln Glu Ala Thr Pro
                 20                  25                  30

Leu Gly Pro Ala Ser Ser Leu Pro Gln Ser Phe Leu Leu Lys Cys Leu
            35                  40                  45

Glu Gln Val Arg Lys Ile Gln Gly Asp Gly Ala Ala Leu Gln Glu Lys
 50                  55                  60

Leu Cys Ala Thr Tyr Lys Leu Cys His Pro Glu Glu Leu Val Leu Leu
 65                  70                  75                  80

Gly His Ser Leu Gly Ile Pro Trp Ala Pro Leu Ser Ser Cys Pro Ser
                 85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
            115                 120                 125

Leu Gly Pro Thr Leu Asp Thr Leu Gln Leu Asp Val Ala Asp Phe Ala
            130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
```

195           200

(2) INFORMATION FOR SEQ ID NO:6:

(i) SEQUENCE CHARACTERISTICS:
        (A) LENGTH: 208 amino acids
        (B) TYPE: amino acid
        (C) STRANDEDNESS: single
        (D) TOPOLOGY: linear (xi) SEQUENCE DESCRIPTION: SEQ ID NO:6:

Met Ala Gln Leu Ser Ala Gln Arg Arg Met Lys Leu Met Ala Leu Gln
1               5                   10                  15

Leu Leu Leu Trp Gln Ser Ala Leu Trp Ser Gly Arg Glu Ala Val Pro
            20                  25                  30

Leu Val Thr Val Ser Ala Leu Pro Pro Ser Leu Pro Leu Pro Arg Ser
        35                  40                  45

Phe Leu Leu Lys Ser Leu Glu Gln Val Arg Lys Ile Gln Ala Ser Gly
    50                  55                  60

Ser Val Leu Leu Glu Gln Leu Cys Ala Thr Tyr Lys Leu Cys His Pro
65                  70                  75                  80

Glu Glu Leu Val Leu Leu Gly His Ser Leu Gly Ile Pro Lys Ala Ser
                85                  90                  95

Leu Ser Gly Cys Ser Ser Gln Ala Leu Gln Gln Thr Gln Cys Leu Ser
            100                 105                 110

Gln Leu His Ser Gly Leu Cys Leu Tyr Gln Gly Leu Leu Gln Ala Leu
        115                 120                 125

Ser Gly Ile Ser Pro Ala Leu Ala Pro Thr Leu Asp Leu Leu Gln Leu
130                 135                 140

Asp Val Ala Asn Phe Ala Thr Thr Ile Trp Gln Gln Met Glu Asn Leu
145                 150                 155                 160

Gly Val Ala Pro Thr Val Gln Pro Thr Gln Ser Ala Met Pro Ala Phe
                165                 170                 175

Thr Ser Ala Phe Gln Arg Arg Ala Gly Gly Val Leu Ala Ile Ser Tyr
            180                 185                 190

Leu Gln Gly Phe Leu Glu Thr Ala Arg Leu Ala Leu His His Leu Ala
        195                 200                 205

(2) INFORMATION FOR SEQ ID NO:7:

(i) SEQUENCE CHARACTERISTICS:
        (A) LENGTH: 212 amino acids
        (B) TYPE: amino acid
        (C) STRANDEDNESS: single
        (D) TOPOLOGY: linear (xi) SEQUENCE DESCRIPTION: SEQ ID NO:7:

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala

```
                        85                  90                  95
Glu Lys Asp Gly Cys Phe Gln Ser Gly Phe Asn Glu Thr Cys Leu
                    100                 105                 110

Val Lys Ile Ile Thr Gly Leu Leu Glu Phe Glu Val Tyr Leu Glu Tyr
                115                 120                 125

Leu Gln Asn Arg Phe Glu Ser Ser Glu Glu Gln Ala Arg Ala Val Gln
130                             135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Asn Ala Ser Leu Leu
                165                 170                 175

Thr Lys Leu Gln Ala Gln Asn Gln Trp Leu Gln Asp Met Thr Thr His
                180                 185                 190

Leu Ile Leu Arg Ser Phe Lys Glu Phe Leu Gln Ser Ser Leu Arg Ala
                195                 200                 205

Leu Arg Gln Met
210
```

(2) INFORMATION FOR SEQ ID NO:8:

(i) SEQUENCE CHARACTERISTICS:
        (A) LENGTH: 211 amino acids
        (B) TYPE: amino acid
        (C) STRANDEDNESS: single
        (D) TOPOLOGY: linear (xi) SEQUENCE DESCRIPTION: SEQ ID NO:8:

```
Met Lys Phe Leu Ser Ala Arg Asp Phe His Pro Val Ala Phe Leu Gly
1               5                   10                  15

Leu Met Leu Val Thr Thr Thr Ala Phe Pro Thr Ser Gln Val Arg Arg
                20                  25                  30

Gly Asp Phe Thr Glu Asp Thr Thr Pro Asn Arg Pro Val Tyr Thr Thr
                35                  40                  45

Ser Gln Val Gly Gly Leu Ile Thr His Val Leu Trp Glu Ile Val Glu
    50                  55                  60

Met Arg Lys Glu Leu Cys Asn Gly Asn Ser Asp Cys Met Asn Asn Asp
65                  70                  75                  80

Asp Ala Leu Ala Glu Asn Asn Leu Lys Leu Pro Glu Ile Gln Arg Asn
                85                  90                  95

Asp Gly Cys Tyr Gln Thr Gly Tyr Asn Gln Glu Ile Cys Leu Leu Lys
                100                 105                 110

Ile Ser Ser Gly Leu Leu Glu Tyr His Ser Tyr Leu Glu Tyr Met Lys
                115                 120                 125

Asn Asn Leu Lys Asp Asn Lys Lys Asp Lys Ala Arg Val Leu Gln Arg
                130                 135                 140

Asp Thr Glu Thr Leu Ile His Ile Phe Asn Gln Glu Val Lys Asp Leu
145                 150                 155                 160

His Lys Ile Val Leu Pro Thr Pro Ile Ser Asn Ala Leu Leu Thr Asp
                165                 170                 175

Lys Leu Glu Ser Gln Lys Glu Trp Leu Arg Thr Lys Thr Ile Gln Phe
                180                 185                 190

Ile Leu Lys Ser Leu Glu Glu Phe Leu Lys Val Thr Leu Arg Ser Thr
                195                 200                 205

Arg Gln Thr
210
```